(12) United States Patent
Steiner

(10) Patent No.: US 7,048,940 B1
(45) Date of Patent: May 23, 2006

(54) ALPHA-PYRONE COMPOSITIONS FOR CONTROLLING CRAVING AND AS A SUBSTITUTE FOR ALCOHOL

(76) Inventor: Gregory Steiner, P.O. Box 61515, Honolulu, HI (US) 96839

( * ) Notice: Subject to any disclaimer, the term of this patent is extended or adjusted under 35 U.S.C. 154(b) by 0 days.

(21) Appl. No.: 09/596,362

(22) Filed: Jun. 17, 2000

Related U.S. Application Data

(60) Provisional application No. 60/141,805, filed on Jun. 29, 1999.

(51) Int. Cl.
*A61K 47/00* (2006.01)
*A61K 35/78* (2006.01)
*A61K 31/335* (2006.01)
*A61K 31/35* (2006.01)

(52) U.S. Cl. .................... 424/439; 424/725; 514/449; 514/451

(58) Field of Classification Search .............. 424/48, 424/444, 464, 440, 400, 404, 451, 455, 439, 424/725; 514/810, 811, 812, 813, 449, 451
See application file for complete search history.

(56) References Cited

U.S. PATENT DOCUMENTS

| 983,998 | A | * | 2/1911 | Holzer | .............. 426/29 |
| 4,661,355 | A | * | 4/1987 | Schur | .............. 426/14 |
| 4,990,350 | A | * | 2/1991 | Rohmann | ......... 426/330.4 |
| 5,234,947 | A | * | 8/1993 | Cherksey | .......... 514/449 |
| 5,332,579 | A | * | 7/1994 | Umbdenstock | ...... 424/639 |
| 5,633,008 | A | * | 5/1997 | Osborne et al. | ...... 424/448 |
| 5,869,505 | A | * | 2/1999 | Keenan | .......... 514/343 |
| 6,025,363 | A | * | 2/2000 | Giles, Jr. | .......... 514/263 |
| 6,045,825 | A | * | 4/2000 | Cody | .......... 424/451 |
| 6,121,289 | A | * | 9/2000 | Houdi | .......... 514/315 |
| 6,174,542 | B1 | * | 1/2001 | Hinton et al. | ......... 424/439 |

FOREIGN PATENT DOCUMENTS

EP   19847134   *   4/2000

OTHER PUBLICATIONS

Kavakaze Internet 1999.*
Bunz NA way Hill looks at it, herbs blend bequtifully. Beverage World Periscope Edition 117(1669):3(1) 1998.*
Goodman & Gilman's The Pharmacological Basis of Therapeutics pp. 562-563 1996.*
Gillmer, R.E. Benzoctamine and oxazepam in the management of alcohol withdrawal states: Comparision by double blind trial South African Medical Journal 47; 2267-2268 1973.*
Kryspine, K. Effect of Kavain on alcoholic patients in withdrawal phase Munchener Medizinishe Woshenschrift 116(36);1557-1560 1974.*
Lemert, E.M. Koni, kona, kava: Orange beer culture of the Cook Islands Journal of Studies on Alcohol 37(5);565-585 1976.*

* cited by examiner

*Primary Examiner*—Michael Hartley
*Assistant Examiner*—Blessing Fubara
(74) *Attorney, Agent, or Firm*—Seth M. Reiss

(57) ABSTRACT

Administered anticraving compositions are disclosed for treating patients addicted to alcohol comprising an effective amount of at least one alpha-pyrone compound formulated into a physiologically acceptable carrier medium. Additionally, a method of oral administration of the anticraving compounds is disclosed where an effective amount of at least one alpha-pyrone compound is formulated into a wine, beer or distilled spirit where the alcohol has been removed and replaced by one or more kavapyrones.

9 Claims, No Drawings

ALPHA-PYRONE COMPOSITIONS FOR CONTROLLING CRAVING AND AS A SUBSTITUTE FOR ALCOHOL

CROSS-REFERENCE TO RELATED APPLICATION

Provisional application No. 60/141,805 filed Jun. 29, 1999

BACKGROUND

1. Field of the Invention

The present invention relates to novel therapeutic compositions comprising at least one alpha-pyrone as the active principal thereof, and to the use of such a method of using compositions for treating cravings and as a substitute for alcohol.

2. Description of Prior Art

Biochemical investigation of addiction has focused on the loci of action of the substance of abuse in the brain. A great deal is known about the receptor sites for the substances of abuse. Many drugs have been designed to react with the receptor sites for substances of abuse in an effort to find an effective treatment for addiction. Considerable knowledge has developed regarding the chemicals produced in the synaptic cleft associated with the substances of abuse and the drugs designed to treat addiction. To date a variety of drugs have been developed in an attempt to control the craving of addiction. However, to date no effective anti-craving medication has been developed in light of the fact that treatment of addiction remains psychological in nature.

Addictions to alcohol and drugs cause great physical and financial harm to the addict and to society. Efforts to develop effective treatments for addictions have been unsuccessful. Temperance and legislative efforts to restrict access to drugs and alcohol have failed.

Alpha-pyrones for the treatment of cravings and/or as a substitute for alcohol have no references in prior art.

SUMMARY OF THE INVENTION

A major object of the present invention is the provision of compounds of the alpha-pyrone type for reducing the craving associated with addiction and compulsive behavior. Another significant object of the present invention is the incorporation of an effective amount of alpha-pyrones in nonalcoholic beer, non-alcoholic wine and non-alcoholic distilled spirits as an effective carrier for the anticraving agents.

In addition, an effective amount of alpha-pyrones added to non-alcoholic beer, non-alcoholic wine and non-alcoholic distilled spirits creates a novel alcohol substitute designed to provide the positive effects of alcohol such as stress reduction and anxiety control without the negative health and social effects of alcoholic beverages.

Briefly, the present invention features novel therapeutic compositions for the treatment of the cravings associated with addictions and compulsive behavior comprising in a physiologically acceptable medium, at least one alpha-pyrone having the following structural formula:

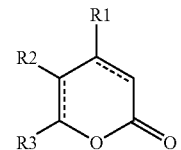

in which R1 is a hydrogen atom or an alkoxy radical having 1 to 4 carbon atoms, R2 is a hydrogen atom or a hydroxyl group, and R3 is an alkyl radical having from 1 to 4 carbon atoms or a styryl or phenethyl radical optionally substituted by one or two methylenedioxy radicals or one or two hydroxyl groups and/or one or two alkoxy radicals having from 1 to 4 carbon atoms, with the proviso that, when R2 is a hydroxyl group, then R3 is necessarily an unsubstituted phenethyl radical, with the future proviso that when R3 is an alkyl radical having 1 to 4 carbon atoms, then R1 and R2 cannot both be hydrogen.

DETAILED DESCRIPTION OF THE INVENTION

The present invention involves administered alpha-pyrones that reduce the cravings of addictions and reduce compulsive behavior. In this invention craving means obsessive compulsion for indulgence in substances that are classed as psychoactive drugs and/or acts which enhances the effect of endogenous and/or exogenous neuropeptides, neorotransmitters and psychoactive agents. Psychoactive drugs include but are not limited alcohol, opiates, stimulants, barbiturates, nicotine and food. Compulsive acts include but are not limited to sexual acts and other compulsive behaviors.

Additionally the invention involves the addition of alpha-pyrones to non-alcoholic beer, non-alcoholic wine and non-alcoholic distilled spirits as an alcohol substitute.

Alpha-pyrones called kavapyrones are naturally found in the kava plant (Piper methysticum). Kava is consumed in order to achieve a relaxed state with a positive mood and a mild euphoria. Kava is intoxicating when large amounts are consumed. However, because kava is nonaddicting (Lebot V. 1992) and does not cause craving or tolerance/dependence, intoxication is essentially unheard-of. The lack of craving and tolerance/dependence results from an effective amount of active alpha-pyrones in kava acting on the dopaminergic neurons of the nucleus accumbens.

The commonly accepted actions of the alpha-pyrones found in kava which are referenced in the literature are as an antianxiety agent (Voltz 1997), antidepressant (Warnecke G et al 1998), euphoriant (Baum S S et al., 1998), muscle relaxant (Seitz 1997), analgesic (Jamieson 1990), anticonvulsant (Kretzschmar R 1969) and as a topical treatment for hair loss (U.S. Pat. No. 558,368). Kava consumption has been found to be directly correlated with a reduction in cancer incidence for a number of South Pacific Nations and is being studied as an effective anticancer agent (unpublished data).

Kavapyrones have become popular in the west as anti-anxiety agents. No side effects have been identified when used on a daily basis in moderate amounts (German Commission E). Years of daily use have been found to cause a dermatologic scaling that is reversed when the drug is discontinued (Norton SA et al., 1994). No irreversible side effects have been noted.

Among the alpha-pyrone compounds comprising the therapeutic compositions of the invention are the following:
1. Kavain
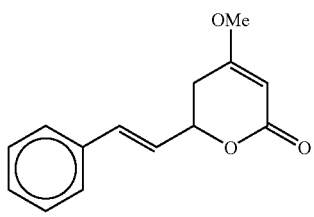
2. 7,8-Dihydrokavain
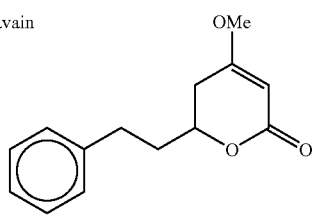
3. 5,6-Dehydrokavain
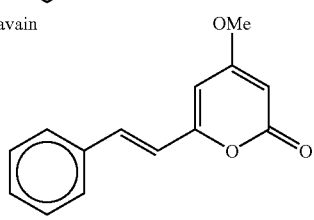
4. Yangonin
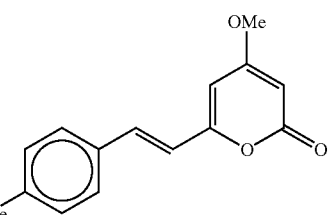
5. 5,6,7,8-Tetrahydroyangonin
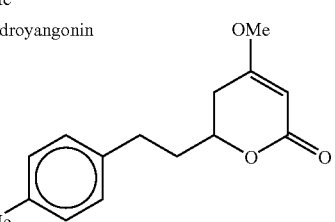
6. Methysticin
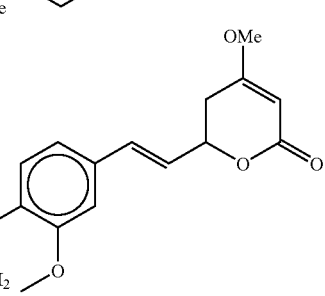
7. Dihydromethysticin
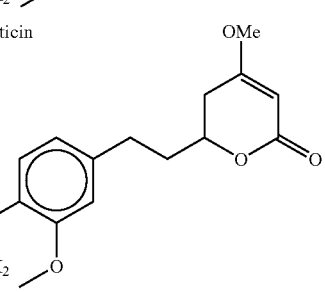
8. 5,6-Dehydromthysticin
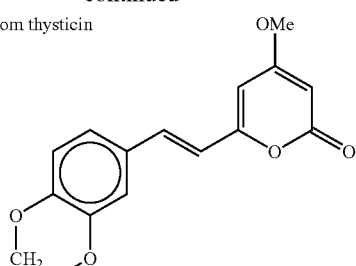
9. 5,6-Dihydroyangonin
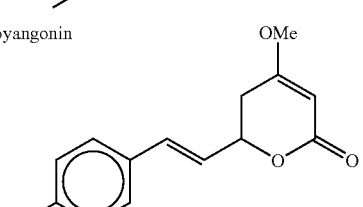
10. 7,8-Dihydroyangonin
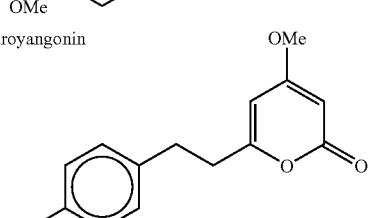
11. 10-Methoxy-yangonin
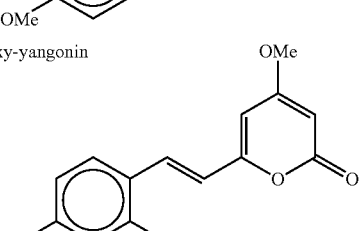
12. Methoxy-yangonin
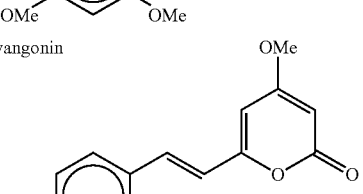
13. 11-Hydroxy-yangonin
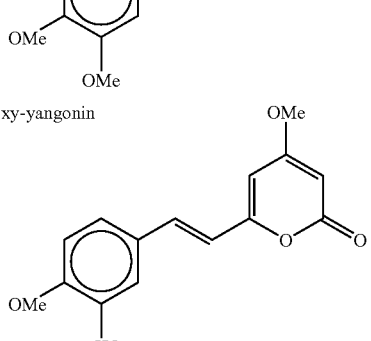
14. Hydroxykavain
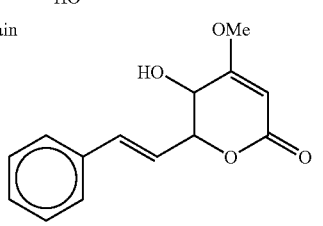

-continued 15. 11-Methyoxy-12-hydroxy-dehydrokavain

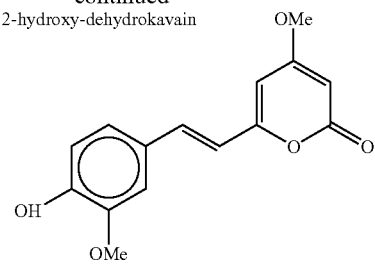

All of these alpha-pyrones compounds are per se known to this art.

The anticraving effects of kavapyrones are mediated through the dopaminergic neurons of the nucleus accumbens in the mesocorticolimbic dopamine reward system. This system is not only responsible for the craving of substances of abuse but is also the same mechanism that produces natural motivation for food, water, sex etc. When kavapyrones are administered in vivo by microdialysis into the nucleus accumbens, increasing doses of kavapyrones produces increased levels of dopamine (Baum, 1998). The kavapyrone desmethoxyyangonin produces an increase in dopamine while the kavapyrone yangonin decreases dopamine to undetectable levels (Baum SS et al., 1998). It is through the mesocorticolimbic dopamine reward system kava increases dopamine in pathways which produce euphoria and an anticraving effect by acting as an antagonist for those dopaminergic neurons responsible for acute craving and its effect on 5-HT (Baum S S et al., 1998).

Kavapyrones are known to influence the function of GABAA receptors. It is through the influence on the GABAA receptor that kava produces anxiolytic effects similar to alcohol, benzodiazepines and barbiturates. However, alcohol, benzodiazepines and barbiturates are known antagonists of NMDA while kava is an agonist (Walden J et al., 1997). This finding supports the fact that kava produces either a mildly stimulating or a mildly sedating effect depending on the preparation and dose. It is also this difference that explains why kava produces little effects on mental and motor function and seldom causes intoxication.

The alpha-pyrone compounds are preferably employed in doses ranging from approximately 5 mg to 600 mg every three to four hours depending on the severity of the craving, the specific alpha-pyrone and the weight of the patient.

Alpha-pyrones known as kavapyrones are present in the plant Piper methysticum. The kavapyrones may be extracted using one of a number of known extraction techniques. These compounds may also be synthesized according to a variety of processes described in the literature.

A physiologically accepted medium used to carry an effective amount of alpha-pyrone can be an inert carrier such as in pill form or as a gum. The physiologically accepted medium used to carry the effective amount of alpha-pyrones in a transdermal patch requires the addition of organic solvents to facilitate transport of the alpha-prone across the skin for systemic distribution.

Addictions are complex physiologic and psychological disorders that require treatment of both the mental and physical aspects of the addiction for success. In alcoholism, it has been found most ideal to not only treat the craving for alcohol but to also satisfy the patients desire for the taste, the feeling and the act of drinking. For this reason a novel aspect of the invention involves the addition of an effective amount of alpha-pyrones to non-alcoholic beer, non-alcoholic wine and non-alcoholic distilled sprits. In this manner the taste, experience and a similar feeling is achieved when drinking the non-alcoholic alpha-pyrone beverage. When an effective amount of alpha-pyrone is substituted for alcohol in beer, wine or distilled sprits patient compliance improves along with the reduction in craving and an improved abstinence from alcohol.

In clinical trails 80% of alcoholics report a resolution of craving for alcohol. In trials for tobacco, cocaine and heroine 100% of the respondents reports a reduction in their craving after consuming an effective amount of alpha-pyrones.

In a double blind placebo controlled study of alcoholics, patients receiving an effective amount of alpha-pyrone achieved abstinence form alcohol more frequently than those taking the placebo (P=0.05).

The most effective physiologically acceptable medium used to carry an effective amount of alpha-pyrone for the treatment of the cravings of alcoholism has been found to be non-alcoholic beverages that mimic the taste, appearance and effect of alcoholic beverages. In this instance the alcoholic patient is not deprived of the enjoyment of his/her beverage of choice and is not required to alter his/her social habits while abstaining form alcohol. The addition of an effective amount of alpha-pyrone for the treatment of craving to non-alcoholic beer, non-alcoholic wine and non-alcoholic distilled sprits provides an ideal delivery medium which produces muscle relaxation, stress reduction, mild euphoria and a reduction in the craving for the substance of abuse.

What is claimed is:

1. A method of treating alcohol craving by administering an anticraving composition of matter, comprising an effective amount of at least one alpha-pyrone compound having the structural formula:

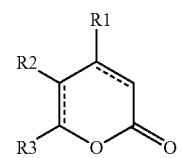

wherein R1 is a hydrogen atom or an alkoxy radical having 1 to 4 carbon atoms, R2 is a hydrogen atom or a hydroxyl group, and R3 is a styryl or phenethyl radical optionally substituted by one or two methylenedioxy radicals or one or two hydroxyl groups and/or one or two alkoxy radicals having from 1 to 4 carbon atoms or one or two alkoxy radicals having from 1 to 4 carbon atoms, with the proviso that, when R2 is a hydroxyl group, then R3 is necessarily an unsubstituted phenethyl radical, in a physiologically acceptable carrier medium.

2. The method of claim 1, wherein said alpha-pyrone compound is one or more of the alpha-pyrones found in the plant Piper methysticum.

3. The method of claim 1, wherein the anticraving composition of matter is administered in the form of a pill.

4. The method of claim 1, wherein the anticraving composition of matter is administered in the form of a gum.

5. The method of claim 1, wherein the anticraving composition of matter is administered in the form of a transdermal patch.

6. The method of claim 1, wherein the anticraving composition of matter is administered in the form of a liquid.

7. The method of claim 1 wherein said anticraving composition is administered orally by way of a non-alcoholic wine beverage.

8. The method of claim 1 wherein said anticraving composition is administered orally by way of a non-alcoholic beer beverage.

9. The method of claim 1 wherein said anticraving composition is administered orally by way of a distilled spirit beverage in regard to which the alcohol has been removed and replaced by kavapyrones.

* * * * *